(12) United States Patent
Noble et al.

(10) Patent No.: US 8,142,886 B2
(45) Date of Patent: Mar. 27, 2012

(54) POROUS LASER SINTERED ARTICLES

(75) Inventors: Aaron M. Noble, Newnan, GA (US);
Guoqiang Mao, Smyrna, GA (US);
Sebastien P. Henry, Smyrna, GA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 133 days.

(21) Appl. No.: 12/179,287

(22) Filed: Jul. 24, 2008

(65) Prior Publication Data

US 2009/0068245 A1 Mar. 12, 2009

Related U.S. Application Data

(60) Provisional application No. 60/961,749, filed on Jul. 24, 2007.

(51) Int. Cl.
*B32B 3/26* (2006.01)
*A61F 2/02* (2006.01)
*B29C 65/16* (2006.01)

(52) U.S. Cl. ............... 428/316.6; 428/310.5; 428/315.5; 428/315.7; 428/317.9; 428/318.4; 623/23.76; 623/23.51; 623/17.16; 264/497

(58) Field of Classification Search ............... 428/315.5, 428/315.7, 316.6, 318.4, 317.9; 623/23.76, 623/23.51, 17.16; 264/497
See application file for complete search history.

(56) References Cited

U.S. PATENT DOCUMENTS

| | | |
|---|---|---|
| 14,403 A | 3/1856 | Brown et al. |
| 222,687 A | 12/1879 | Fresco |
| 2,373,769 A | 4/1945 | Macy |
| 3,520,099 A | 7/1970 | Mattes |
| 3,556,918 A | 1/1971 | Lemelson |
| 3,605,123 A | 9/1971 | Pratt et al. |
| 3,806,961 A | 4/1974 | Muller |
| 3,816,855 A | 6/1974 | Saleh |
| 3,826,054 A | 7/1974 | Culpepper, Jr. |
| 4,047,349 A | 9/1977 | Aguilar, Jr. |
| 4,085,466 A | 4/1978 | Goodfellow et al. |
| 4,154,040 A | 5/1979 | Pace |
| 4,164,794 A | 8/1979 | Spector et al. |
| 4,202,055 A | 5/1980 | Reiner et al. |
| 4,218,494 A | 8/1980 | Belmondo et al. |
| 4,305,340 A | 12/1981 | Iwaki et al. |
| 4,344,193 A | 8/1982 | Kenny |

(Continued)

FOREIGN PATENT DOCUMENTS

CA 2295896 A1 7/2000

(Continued)

OTHER PUBLICATIONS

PCT/US2008/008955 International Search Report and Written Opinion mailed Dec. 3, 2008.

(Continued)

*Primary Examiner* — Hai Vo
(74) *Attorney, Agent, or Firm* — Lerner, David, Littenberg, Krumholz & Mentlik, LLP

(57) ABSTRACT

The present invention provides selectively laser sintered porous polymeric articles and methods of making and using the same. In one embodiment, a method of the present invention comprises providing a first layer of particles of a first polymeric material, heating selected locations of the first layer to sinter particles of the first polymeric material to form a three-dimensional article, the three-dimensional article having a porosity of at least about 30 percent.

25 Claims, 3 Drawing Sheets

U.S. PATENT DOCUMENTS

| | | |
|---|---|---|
| 4,385,404 A | 5/1983 | Sully et al. |
| 4,444,818 A | 4/1984 | Tominaga et al. |
| 4,502,161 A | 3/1985 | Wall |
| 4,513,045 A | 4/1985 | Bondoc et al. |
| 4,543,158 A | 9/1985 | Bondoc et al. |
| 4,636,219 A | 1/1987 | Pratt et al. |
| 4,644,942 A | 2/1987 | Sump |
| 4,673,408 A | 6/1987 | Grobbelaar |
| 4,714,473 A | 12/1987 | Bloebaum |
| 4,714,474 A | 12/1987 | Brooks, Jr. et al. |
| 4,719,908 A | 1/1988 | Averill et al. |
| 4,766,029 A | 8/1988 | Brock et al. |
| 4,863,538 A | 9/1989 | Deckard |
| 4,944,817 A | 7/1990 | Bourell et al. |
| 4,961,154 A | 10/1990 | Pomerantz et al. |
| 4,969,302 A | 11/1990 | Coggan et al. |
| 4,969,907 A | 11/1990 | Koch et al. |
| 4,990,163 A | 2/1991 | Ducheyne et al. |
| 5,004,476 A | 4/1991 | Cook |
| 5,017,753 A | 5/1991 | Deckard |
| 5,024,670 A | 6/1991 | Smith et al. |
| 5,031,120 A | 7/1991 | Pomerantz et al. |
| 5,034,186 A | 7/1991 | Shimamune et al. |
| 5,053,090 A | 10/1991 | Beaman et al. |
| 5,067,964 A | 11/1991 | Richmond et al. |
| 5,076,869 A | 12/1991 | Bourell et al. |
| 5,080,674 A | 1/1992 | Jacobs et al. |
| 5,090,174 A | 2/1992 | Fragale |
| 5,108,432 A | 4/1992 | Gustavson |
| 5,108,441 A | 4/1992 | McDowell |
| 5,147,402 A | 9/1992 | Bohler et al. |
| 5,155,324 A | 10/1992 | Deckard et al. |
| 5,158,574 A | 10/1992 | Stone |
| 5,171,282 A | 12/1992 | Pequignot |
| 5,176,710 A | 1/1993 | Hahn et al. |
| 5,192,328 A | 3/1993 | Winters |
| 5,219,362 A | 6/1993 | Tuke et al. |
| 5,282,861 A | 2/1994 | Kaplan |
| 5,282,870 A | 2/1994 | Moser et al. |
| 5,287,435 A | 2/1994 | Cohen et al. |
| 5,314,478 A | 5/1994 | Oka et al. |
| 5,323,954 A | 6/1994 | Shetty et al. |
| 5,336,518 A | 8/1994 | Narayanan et al. |
| 5,356,433 A | 10/1994 | Rowland et al. |
| 5,358,529 A | 10/1994 | Davidson |
| 5,368,602 A | 11/1994 | de la Torre |
| 5,386,500 A | 1/1995 | Pomerantz et al. |
| 5,398,193 A | 3/1995 | deAngelis |
| 5,425,210 A | 6/1995 | Zafir |
| 5,443,510 A | 8/1995 | Shetty et al. |
| 5,443,518 A | 8/1995 | Insall |
| 5,461,839 A | 10/1995 | Beck |
| 5,486,599 A | 1/1996 | Saunders et al. |
| 5,490,962 A | 2/1996 | Cima et al. |
| 5,496,372 A | 3/1996 | Hamamoto et al. |
| 5,504,300 A | 4/1996 | Devanathan et al. |
| 5,514,183 A | 5/1996 | Epstein et al. |
| 5,526,627 A | 6/1996 | Beck |
| 5,549,700 A | 8/1996 | Graham et al. |
| 5,571,185 A | 11/1996 | Schug |
| 5,571,196 A | 11/1996 | Stein |
| 5,609,646 A | 3/1997 | Field et al. |
| 5,616,294 A | 4/1997 | Deckard |
| 5,624,463 A | 4/1997 | Stone et al. |
| 5,632,745 A | 5/1997 | Schwartz |
| 5,640,667 A | 6/1997 | Freitag et al. |
| 5,648,450 A * | 7/1997 | Dickens et al. ............... 528/323 |
| 5,681,354 A | 10/1997 | Eckhoff |
| 5,702,448 A | 12/1997 | Buechel et al. |
| 5,728,162 A | 3/1998 | Eckhoff |
| 5,729,946 A | 3/1998 | Beck |
| 5,735,903 A | 4/1998 | Li et al. |
| 5,749,874 A | 5/1998 | Schwartz |
| 5,769,899 A | 6/1998 | Schwartz et al. |
| 5,773,789 A | 6/1998 | Devanathan et al. |
| 5,776,201 A | 7/1998 | Colleran et al. |
| 5,782,908 A | 7/1998 | Cahalan et al. |
| 5,795,353 A | 8/1998 | Felt |
| 5,824,098 A | 10/1998 | Stein |
| 5,824,102 A | 10/1998 | Buscayret |
| 5,839,247 A | 11/1998 | Beck |
| 5,857,303 A | 1/1999 | Beck et al. |
| 5,866,113 A | 2/1999 | Hendriks et al. |
| 5,879,387 A | 3/1999 | Jones et al. |
| 5,879,398 A | 3/1999 | Swarts et al. |
| 5,928,285 A | 7/1999 | Bigliani et al. |
| 5,973,222 A | 10/1999 | Devanathan et al. |
| 5,987,838 A | 11/1999 | Beck |
| 5,989,472 A | 11/1999 | Ashby et al. |
| 6,013,855 A | 1/2000 | McPherson et al. |
| 6,046,426 A | 4/2000 | Jeantette et al. |
| 6,049,054 A | 4/2000 | Panchison et al. |
| 6,087,553 A | 7/2000 | Cohen et al. |
| 6,096,043 A | 8/2000 | Techiera et al. |
| 6,128,866 A | 10/2000 | Wearne |
| 6,132,468 A | 10/2000 | Mansmann |
| 6,139,585 A | 10/2000 | Li |
| 6,164,032 A | 12/2000 | Beck |
| 6,171,340 B1 | 1/2001 | McDowell |
| 6,190,407 B1 | 2/2001 | Ogle et al. |
| 6,206,924 B1 | 3/2001 | Timm |
| 6,206,927 B1 | 3/2001 | Fell et al. |
| 6,215,093 B1 | 4/2001 | Meiners et al. |
| 6,248,131 B1 | 6/2001 | Felt et al. |
| 6,251,143 B1 | 6/2001 | Schwartz et al. |
| 6,261,322 B1 | 7/2001 | Despres, III et al. |
| 6,280,478 B1 | 8/2001 | Richter et al. |
| 6,283,997 B1 | 9/2001 | Garg et al. |
| 6,299,645 B1 | 10/2001 | Ogden |
| 6,344,061 B1 | 2/2002 | Leitao et al. |
| 6,355,086 B2 | 3/2002 | Brown et al. |
| 6,370,382 B1 | 4/2002 | Kang et al. |
| 6,371,958 B1 | 4/2002 | Overaker |
| 6,385,585 B1 | 5/2002 | Jonsson et al. |
| 6,395,327 B1 | 5/2002 | Shetty |
| 6,406,497 B2 | 6/2002 | Takei |
| 6,415,574 B2 | 7/2002 | Beck |
| 6,454,811 B1 * | 9/2002 | Sherwood et al. ......... 623/23.76 |
| 6,476,343 B2 | 11/2002 | Keicher et al. |
| 6,482,209 B1 | 11/2002 | Engh et al. |
| 6,494,914 B2 | 12/2002 | Brown et al. |
| 6,520,996 B1 | 2/2003 | Manasas et al. |
| 6,530,951 B1 | 3/2003 | Bates et al. |
| 6,551,608 B2 * | 4/2003 | Yao ............................. 424/409 |
| 6,558,421 B1 | 5/2003 | Fell et al. |
| 6,582,715 B1 | 6/2003 | Barry et al. |
| 6,589,283 B1 | 7/2003 | Metzger et al. |
| 6,592,598 B2 | 7/2003 | Vibe-Hansen et al. |
| 6,599,301 B2 | 7/2003 | Vibe-Hansen et al. |
| 6,610,067 B2 | 8/2003 | Tallarida et al. |
| 6,626,945 B2 | 9/2003 | Simon et al. |
| 6,632,246 B1 | 10/2003 | Simon et al. |
| 6,652,246 B1 | 11/2003 | Lin et al. |
| 6,652,587 B2 | 11/2003 | Felt et al. |
| 6,679,917 B2 | 1/2004 | Ek |
| 6,682,567 B1 | 1/2004 | Schroeder |
| 6,686,437 B2 | 2/2004 | Buchman et al. |
| 6,699,252 B2 | 3/2004 | Farr, II et al. |
| 6,709,462 B2 | 3/2004 | Hanssen |
| 6,712,822 B2 | 3/2004 | Re et al. |
| 6,712,856 B1 | 3/2004 | Carignan et al. |
| 6,716,957 B2 | 4/2004 | Tunc |
| 6,743,232 B2 | 6/2004 | Overaker et al. |
| 6,770,099 B2 | 8/2004 | Andriacchi et al. |
| 6,846,329 B2 | 1/2005 | McMinn |
| 6,850,125 B2 | 2/2005 | Norman et al. |
| 6,852,125 B2 | 2/2005 | Simon et al. |
| 6,855,165 B2 | 2/2005 | Fell et al. |
| 6,863,689 B2 | 3/2005 | Ralph et al. |
| 6,866,684 B2 | 3/2005 | Fell et al. |
| 6,893,463 B2 | 5/2005 | Fell et al. |
| 6,911,044 B2 | 6/2005 | Fell et al. |
| 6,916,341 B2 | 7/2005 | Rolston |
| 6,921,264 B2 | 7/2005 | Mayer et al. |
| 6,923,831 B2 | 8/2005 | Fell et al. |
| 6,932,610 B2 | 8/2005 | Ono et al. |
| 7,168,283 B2 | 1/2007 | Van Note et al. |

| | | | |
|---|---|---|---|
| 7,494,507 B2 | 2/2009 | Dixon et al. | |
| 7,674,517 B2 | 3/2010 | Ramsey et al. | |
| 2001/0014403 A1 | 8/2001 | Brown et al. | |
| 2002/0010512 A1 | 1/2002 | Takei | |
| 2002/0015654 A1 | 2/2002 | Das et al. | |
| 2002/0016635 A1 | 2/2002 | Despres et al. | |
| 2002/0127328 A1 | 9/2002 | Shetty | |
| 2002/0130112 A1 | 9/2002 | Manasas et al. | |
| 2002/0151983 A1 | 10/2002 | Shetty | |
| 2002/0173855 A1 | 11/2002 | Mansmann | |
| 2002/0198528 A1 | 12/2002 | Engh et al. | |
| 2003/0032351 A1 | 2/2003 | Horner et al. | |
| 2003/0033018 A1 | 2/2003 | Merchant | |
| 2003/0045941 A1 | 3/2003 | Lewallen | |
| 2003/0055500 A1 | 3/2003 | Fell et al. | |
| 2003/0055501 A1 | 3/2003 | Fell et al. | |
| 2003/0060882 A1 | 3/2003 | Fell et al. | |
| 2003/0060883 A1 | 3/2003 | Fell et al. | |
| 2003/0060884 A1 | 3/2003 | Fell et al. | |
| 2003/0060885 A1 | 3/2003 | Fell et al. | |
| 2003/0060888 A1 | 3/2003 | Fell et al. | |
| 2003/0069638 A1 | 4/2003 | Barlow et al. | |
| 2003/0069718 A1 | 4/2003 | Hollister et al. | |
| 2003/0153977 A1 | 8/2003 | Suguro et al. | |
| 2003/0153981 A1 | 8/2003 | Wang et al. | |
| 2003/0155686 A1 | 8/2003 | Hawkins et al. | |
| 2003/0158606 A1 | 8/2003 | Coon et al. | |
| 2003/0209305 A1 | 11/2003 | Smith et al. | |
| 2003/0220696 A1 | 11/2003 | Levine et al. | |
| 2004/0006393 A1 | 1/2004 | Burkinshaw | |
| 2004/0009228 A1 | 1/2004 | Tormala et al. | |
| 2004/0015170 A1 | 1/2004 | Tallarida et al. | |
| 2004/0023586 A1 | 2/2004 | Tilton | |
| 2004/0044414 A1 | 3/2004 | Nowakowski | |
| 2004/0054416 A1 | 3/2004 | Wyss et al. | |
| 2004/0059356 A1 | 3/2004 | Gingras | |
| 2004/0098132 A1 | 5/2004 | Andriacchi et al. | |
| 2004/0121110 A1 | 6/2004 | Schmidt et al. | |
| 2004/0143339 A1 | 7/2004 | Axelson et al. | |
| 2004/0148030 A1 | 7/2004 | Ek | |
| 2004/0153163 A1 | 8/2004 | Posner | |
| 2004/0162622 A1 | 8/2004 | Simon et al. | |
| 2004/0167633 A1 | 8/2004 | Wen et al. | |
| 2004/0191106 A1 | 9/2004 | O'Neill et al. | |
| 2004/0199249 A1 | 10/2004 | Fell | |
| 2004/0199250 A1 | 10/2004 | Fell | |
| 2004/0204766 A1 | 10/2004 | Siebel | |
| 2004/0230315 A1 | 11/2004 | Ek | |
| 2004/0243237 A1 | 12/2004 | Unwin et al. | |
| 2004/0267363 A1 | 12/2004 | Fell et al. | |
| 2005/0033424 A1 | 2/2005 | Fell | |
| 2005/0043816 A1 | 2/2005 | Datta et al. | |
| 2005/0079200 A1 | 4/2005 | Rathenow et al. | |
| 2005/0085918 A1 | 4/2005 | Soffiati et al. | |
| 2005/0100578 A1* | 5/2005 | Schmid et al. | 424/423 |
| 2005/0123672 A1 | 6/2005 | Justin et al. | |
| 2005/0154471 A1 | 7/2005 | Aram et al. | |
| 2005/0170159 A1* | 8/2005 | Ramsey et al. | 428/212 |
| 2005/0171604 A1 | 8/2005 | Michalow | |
| 2005/0177169 A1 | 8/2005 | Fisher et al. | |
| 2005/0192672 A1 | 9/2005 | Wyss et al. | |
| 2006/0036331 A1* | 2/2006 | Lu et al. | 623/23.51 |
| 2006/0045903 A1* | 3/2006 | Kadiyala et al. | 424/426 |
| 2006/0147332 A1 | 7/2006 | Jones et al. | |
| 2007/0142914 A1 | 6/2007 | Jones et al. | |
| 2007/0156249 A1 | 7/2007 | Lawrynowicz et al. | |
| 2007/0225390 A1* | 9/2007 | Wang et al. | 521/77 |
| 2008/0004709 A1 | 1/2008 | O'Neill et al. | |
| 2008/0050412 A1 | 2/2008 | Jones et al. | |
| 2008/0161927 A1* | 7/2008 | Savage et al. | 623/17.16 |
| 2009/0068245 A1 | 3/2009 | Noble et al. | |
| 2009/0087605 A1* | 4/2009 | Ramsey et al. | 428/36.5 |

FOREIGN PATENT DOCUMENTS

| | | |
|---|---|---|
| DE | 19502733 A1 | 3/1996 |
| EP | 0 178 650 A2 | 4/1986 |
| EP | 0295038 A2 | 12/1988 |
| EP | 0 528 800 A1 | 3/1993 |
| EP | 0761242 A1 | 3/1997 |
| EP | 1 300 511 A2 | 4/2003 |
| EP | 1418013 A1 | 5/2004 |
| EP | 1426013 A1 | 6/2004 |
| EP | 1455666 A1 | 9/2004 |
| EP | 1493455 A2 | 1/2005 |
| EP | 1683593 A2 | 7/2006 |
| EP | 1806154 A1 | 7/2007 |
| EP | 1949989 | 7/2008 |
| JP | 2255329 A | 10/1990 |
| JP | 4041794 A | 2/1992 |
| JP | 11287020 A | 10/1999 |
| JP | 2001303751 A | 10/2001 |
| RU | 2218242 C2 | 12/2003 |
| WO | WO-96/06881 | 3/1996 |
| WO | 2005/084216 A2 | 9/2005 |
| WO | 2005087982 A1 | 9/2005 |
| WO | WO-2007/058160 | 5/2007 |

OTHER PUBLICATIONS

PCT/US2008/008955 International Preliminary Report on Patentability mailed Feb. 4, 2010.
"Direct Generation of Metal Parts and Tools by Selective Laser Powder Remelting (SLPR)", W. Meiners, C. Over, K. Wissenbach, R. Poprawe, pp. 655-661.
C.K. Chua et al. Development of a Tissue Engineering Scaffold Structure Library for Rapid Prototyping. Parts 1 and 2, International Journal of Advanced Manufacturing Technology, (2003) vol. 21, pp. 291-312.
Created and Designed by Shaman Gaspar, Maintained by Peter Fox, "Direct Laser Remelting", "Project Web Site", Using Lasers to Grow 3D object on Stainless Steel; The University of Liverpool 2002; http://mserc.liv.ac.uk/research/dlr/dlr__html.
Dr. Kerron Harvey, producer, Research Intelligence, The University of Liverpool, Issue 13, Jun. 2002.
European Search Report and Written Opinion, EP05028133, dated May 11, 2010.
European Search Report and Written Opinion, EP06127218, dated May 6, 2010.
European Search Report and Written Opinion, EP10162970, dated Jun. 17, 2010.
H.J. Niu and I.T.H. Chang, "Selective Laser Sintering of Gas and Water Atomized High Speed Steel Powders," Scripta Materialia vol. 41, No. 1, (1999), pp. 25-30.
Hawley's Condensed Chemical Dictionary, 14th edition. John Wiley & Sons, 2002. Definition: sintering.
Hollander et al., Structural mechanical and in vitro characterization of individually structured Ti-Al-4V produces by direct layer forming, Biomaterials, pp. 1-9, 2005.
Meiners W, Over C, Wissenbach K, Poprawe R., Direct generation of metal parts and tools by selective laser powder remelting (SLPR). Proceedings of SFF, Austin, Texas, Aug. 9-11, 1999.
N.K. Vail, L.D. Swain, W.C. fox, T.B. Aufdlemorte, G. Lee, J.W. Barlow, "Materials for biomedical applications," Materials and Design, 20, 1999, pp. 123-132.
Patello-femoral Arthroplasty X-ray Results, Stryker Howmedica Osteonics, date not known.
R. Morgan, C.J. Sutcliffe, W. O'Neill, "Experimental investigatoin of nanosecond pulsed Nd:YAG laser re-melted pre-placed powder beds," Rapid Prototyping Journal, vol. 7, No. 3, 2001, pp. 159-172.
R.H. Morgan, A.J. Papworth, C. Sutcliffe, P. Fox, W. O'Neill, "High density net shape components by direct laser re-melting of single phase powders," Journal of Materials Science, 37, 2002, pp. 3093-3100.
The Metals Handbook, Desk Edition, 2nd Edition, ASM International, 1998, p. 29.
Vureal et al., Plasma-sprayed oxide ceramics on steel substrates, Surface Coatings and Technology, 97 (1997) 347-354.

* cited by examiner

US 8,142,886 B2

POROUS LASER SINTERED ARTICLES

CROSS-REFERENCE TO RELATED APPLICATIONS

This application claims the benefit of the filing date of U.S. Provisional Patent Application No. 60/961,749 filed Jul. 24, 2007, the disclosure of which is hereby incorporated herein by reference.

FIELD OF THE INVENTION

The present invention relates to sintered polymeric materials and, in particular, to laser sintered porous polymeric materials.

BACKGROUND OF THE INVENTION

Laser sintering is a process involving the construction of a three-dimensional article by selectively projecting a laser beam having the desired energy onto a layer of particles. When coupled with computer aided design apparatus, selective laser sintering is an effective technique for producing prototype as well as mainstream production articles.

Sintered porous polymeric articles are currently constructed by traditional heat sintering processes. Traditional heat sintering processes include fabricating a mold having the desired shape of the article to be produced, filling the mold with powder, heating the mold to sinter the powder particles therein, cooling the mold, and removing the formed article. The requirement of a mold in traditional sintering processes can be a limiting factor in the production of prototype articles as well as articles with complicated shapes. The need to construct a mold can make prototype development expensive and time consuming. Moreover, molds are limited to some extent by the structural complexity of the article to be produced and often require the use of release agents for effective removal of the article from the mold. Release agents are generally undesirable for applications where purity or cleanliness of the produced article is of importance.

With continuing advances in imaging and computer aided design, increasingly complex articles are being developed for production. Reconstructive implants and prosthetic devices, among other areas, have benefited from such advances leading to the design of implants unique to the individual needs of patients. Computer imaging such computed tomography (CT), for example, can permit the design of a custom reconstructive implant operable to match the physical parameters of an individual patient. Nevertheless, due to the limitations of traditional mold sintering processes discussed above, actual fabrication of a porous sintered implant having a complicated or custom shape can be difficult or impracticable.

SUMMARY OF THE INVENTION

The present invention provides laser sintered porous polymeric articles and methods of making and using the same. In some embodiments, a laser sintered porous polymeric article comprises an implant tailored to the physical parameters of an individual patient, such as a craniofacial or maxillofacial implant. Moreover, in some embodiments, methods of the present invention permit the design and fabrication of sintered porous polymeric articles having custom and/or complicated shapes or structures, such as implants. Porous sintered polymeric articles produced according to methods of the present invention, in some embodiments, are free or substantially free from foreign materials such as those introduced in traditional mold sintering processes.

In one embodiment, the present invention provides a laser sintered porous polymeric article having an average pore size ranging from about 10 μm to about 1 mm. In some embodiments, a laser sintered porous polymeric article has an average pore size of at least about 20 μm. A laser sintered porous polymeric article, in some embodiments, has a porosity ranging from about 20 percent to about 60 percent. In some embodiments, a laser sintered porous polymeric material comprises multidirectional and/or interconnected pores. Additionally, in some embodiments, a laser sintered porous polymeric article comprises only a single sintered polymeric layer.

The porous structure of laser sintered porous polymeric articles of the present invention fundamentally differs from laser sintered articles in the prior art. Laser sintered polymeric articles of the prior art, such as those used in prototype applications, are fabricated under conditions that eliminate or minimize porosity and pore structure. As understood by one of skill in the art, pore structure and porosity are generally undesirable properties in a laser sintered prototype article, which detract from the quality of the article. Laser sintered polymeric articles, therefore, are often constructed using polymers having high melt flow indices unsuitable for producing a porous structure. The high melt flow polymeric materials simply melt to form a non-porous product during the sintering process.

In another embodiment, the present invention provides a laser sintered porous polymeric article comprising a first layer and at least one additional layer. In some embodiments, the first layer and the at least one additional layer comprise the same polymeric material. In other embodiments, the first layer and the at least one additional layer comprise different polymeric materials. Moreover, in one embodiment, the first layer has a porosity greater than the at least one additional layer. Alternatively, in another embodiment, the first layer has a porosity less than the at least one additional layer.

In some embodiments, the first and/or any additional layer is non-porous or substantially non-porous. In one embodiment, for example, a laser sintered porous polymeric article comprises a porous surface layer and a non-porous or substantially non-porous second layer. A non-porous or substantially non-porous second layer, in some embodiments, is the core of the laser sintered article. In such embodiments, the porous surface layer envelopes the non-porous core. In other embodiments, the porous surface layer partially covers the non-porous core.

Laser sintered porous polymeric articles, in some embodiments of the present invention, further comprise at least one inorganic material. In some embodiments, a laser sintered porous polymeric article further comprises a plurality of particles of at least one inorganic material dispersed throughout the article. In one embodiment, an inorganic material comprises a metal including, but not limited to, a transition metal, such as titanium, silver or mixtures thereof. In another embodiment, an inorganic material comprises surgical grade stainless steel, steel coated with titanium, titanium nitride, or titanium alloyed with other metals. In a further embodiment, an inorganic material comprises a calcium phosphate. In one embodiment, an inorganic material comprises a glass. In some embodiments, a glass has a composition comprising by weight 45% $SiO_2$, 24.5% $Na_2O$, 24.5% CaO, and 6% $P_2O_5$. In some embodiments, a glass comprises BIOGLASS® commercially available from NovaBone Products, LLC of Alachua Fla. or a hydroxyapatite. In some embodiments, an inorganic material comprises a mixture of any of the foregoing metals, alloys, calcium phosphates, and/or glasses.

In some embodiments, a laser sintered porous polymeric article does not comprise an inorganic material, including metals and/or ceramics, in any amount or substantially any amount.

Additionally, laser sintered porous polymeric articles, in some embodiments of the present invention, are implants including, but not limited to, non-load bearing implants and/or load bearing implants. In one embodiment, a laser sintered porous polymeric article is a craniofacial implant or a maxillofacial implant. Implants, according to some embodiments of the present invention, may be used to repair any portion of the cranium, such as the frontal, occipital, parietal, and temporal bones, portions thereof, or combinations thereof. Implants of the present invention, may also be used to repair other bones of the face, such as the maxilla and mandible. In another embodiment, implants of the present invention include hip implants, spine implants as well as other implants for load bearing applications in the body.

In another aspect, the present invention provides methods of making a laser sintered porous polymeric article. A method of making a laser sintered porous polymeric article, in one embodiment, comprises providing a first layer of particles of a first polymeric material, heating selected locations of the first layer with electromagnetic radiation to sinter particles of the first polymeric material to form a three-dimensional article, the three-dimensional article having an average pore size of at least 20 µm. In some embodiments, the three-dimensional article has an average pore size ranging from about 10 µm to about 1 mm. In some embodiments, the sintered porous three-dimensional article has a porosity ranging from about 20 percent to about 60 percent. In another embodiment, the sintered porous three-dimensional article has a porosity of at least about 20 percent. In some embodiments, the sintered porous three-dimensional article has a porosity of at least about 30 percent.

In some embodiments, the first layer of particles of a first polymeric material has a thickness greater than about 10 µm, greater than about 50 µm, greater than about 75 µm, greater than about 100 µm, greater than about 200 µm, or greater than 500 µm.

In some embodiments of methods of making a laser sintered porous polymeric material, electromagnetic radiation comprises visible electromagnetic radiation, infrared electromagnetic radiation, or combinations thereof. Moreover, in embodiments of methods of the present invention, electromagnetic radiation is supplied from a radiation source. In one embodiment, a radiation source comprises a laser. Lasers suitable for use in some embodiments of the present invention comprise gas lasers, such as a carbon dioxide ($CO_2$) laser, solid state lasers, such as a Nd:YAG (neodymium-doped yttrium aluminium garnet; $Nd:Y_3Al_5O_{12}$) laser, or semiconductor lasers, such as a laser diode.

A laser sintered porous three-dimensional article, in one embodiment, comprises an implant as provided herein. An implant, in some embodiments, comprises a non-load bearing implant, such as a craniofacial implant or maxillofacial implant. An implant, in other embodiments, comprises a load bearing implant, such as a hip implant or a spinal implant.

A method of making a laser sintered porous polymeric article, in some embodiments, further comprises providing at least one additional layer of particles of an additional polymeric material adjacent to the first layer and heating selected locations of the at least one additional layer with electromagnetic radiation to sinter particles of the additional polymeric material. In some embodiments, the first polymeric material and the additional polymeric material are the same. In other embodiments, the first polymeric material and the additional polymeric material are different.

Each additional layer comprising particles of an additional polymeric material, according to some embodiments of the present invention, is stacked upon the preceding layer in order increase the thickness of the laser sintered porous polymeric article. Sintered locations of each additional layer, in some embodiments, are selected to correspond with sintered locations of the preceding layer such that each additional layer and the preceding layer are fused together. Any number of additional layers may be stacked to produce a laser sintered porous polymeric article having any desired thickness. In some embodiments, each additional layer has a thickness of greater than about 10 µm, greater than about 50 µm, greater than about 75 µm, greater than about 100 µm, greater than about 200 µm or greater than about 500 µm.

Furthermore, in some embodiments of methods of making a sintered porous polymeric article, the first layer has a porosity greater than the at least one additional layer. Alternatively, in other embodiments, the at least one additional layer has a porosity greater than the first layer.

In some embodiments, at least one the first and second layers is non-porous or substantially non-porous. In one embodiment, for example, a laser sintered porous polymeric article comprises a porous surface layer and a non-porous or substantially non-porous second layer. A non-porous or substantially non-porous second layer, in some embodiments, is the core of the laser sintered article. In such embodiments, the porous surface layer envelopes the non-porous core. In other embodiments, the porous surface layer partially covers the non-porous core.

In some embodiments of methods of the present invention, particles of a first polymeric material are mixed with particles of at least one inorganic material prior to sintering. In other embodiments, particles of the additional polymeric material are mixed with particles of at least one inorganic material prior to sintering.

In some embodiments, a method of making a laser sintered porous polymeric article further comprises heating the article subsequent to formation. In some embodiments, the laser sintered porous article, once formed, is heated to a temperature near or above the melting point of the first polymeric material and/or any additional polymeric material. Moreover, the time period for heating is dependent on the size of the article and, in some embodiments, ranges from about 30 second to about 60 minutes. A laser sintered porous article, in some embodiments, is heated in an oven.

Additionally, in some embodiments, methods of making a laser sintered porous polymeric article further comprises smoothing one or more surfaces of the article. Smoothing one or more surfaces of a laser sintered porous polymeric article can be accomplished by a variety of processes, including tumbling, sanding, or combinations thereof.

In a further aspect, the present invention provides methods of treating patients in need of an implant. In one embodiment, a method of treating a patient in need of an implant comprises creating a three-dimensional image of an implant area in the patient, converting the three-dimensional image into a format compatible with a selective laser sintering apparatus, providing a first layer of particles of a first polymeric material, heating locations of the first layer selected according to the three-dimensional image with electromagnetic radiation to sinter particles of the first polymeric material to form a three-dimensional implant having an average pore size of at least about 20 µm, and inserting the three dimensional implant into the implant area of the patient In some embodiments, the three-dimensional implant has an average porosity ranging from about 20 percent to about 60 percent. In another embodiment, the three-dimensional implant has an average porosity of at least about 20 percent. In some embodiments, the three-dimensional article has an average porosity of at least about 30 percent. Moreover, three-dimensional implants of the present invention can be inserted into the implant area of a patient according to techniques known to one of skill in the art.

Implants for use in methods of treating patients in need thereof, in some embodiments, comprise at least one additional layer of sintered polymeric particles. As a result, a method of treating a patient in need of an implant, in some embodiments, further comprises providing at least one additional layer of particles of an additional polymeric material adjacent to the first layer and heating locations of the at least one additional layer selected according to the three-dimensional image with electromagnetic radiation to sinter particles of the additional polymeric material. In some embodiments, the first polymeric material and the additional polymeric material are the same. In other embodiments, the first polymeric material and the additional polymeric material are different.

Moreover, in some embodiments of methods of treating a patient in need of an implant, the first layer of particles of a first polymeric material has a thickness greater than about 10 µm, greater than about 50 µm, greater than about 75 µm, greater than about 100 µm, greater than about 200 µm, or greater than about 500 µm. In some embodiments, each additional layer of particles of an additional polymeric material has a thickness greater than about 10 µm, greater than about 50 µm, greater than about 75 µm, greater than about 100 µm, or greater than about 200 µm or greater than about 500 µm.

In some embodiments, the three-dimensional implant is a non-load bearing implant. In other embodiments, the three-dimensional implant is a load bearing implant. In one embodiment, for example, the three-dimensional implant is a maxillofacial implant or a craniofacial implant. In some embodiments, the implant is a hip implant or a spinal implant.

These and other embodiments of the present invention are described in greater detail in the detailed description which follows. These and other objects, features and advantages of the present invention will become apparent after a review of the following detailed description of the disclosed embodiments and claims.

DETAILED DESCRIPTION

Figure 1:
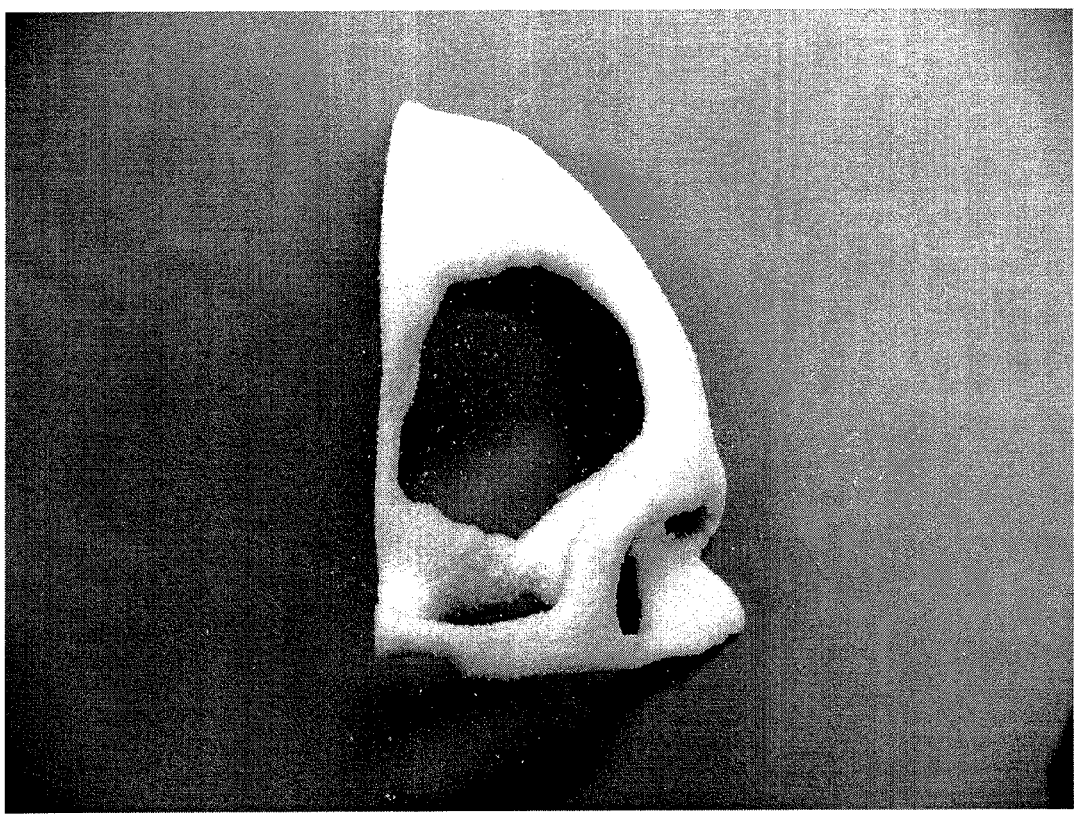
FIG. 1 illustrates a perspective view of a laser sintered porous polymeric article according to one embodiment of the present invention.

The present invention provides laser sintered porous polymeric articles and methods of making and using the same. Laser sintered porous polymeric articles of the present invention can demonstrate structures or shapes too complicated or impracticable for traditional heat sintering techniques requiring the fabrication and use of a mold. Moreover, laser sintered porous polymeric articles of the present invention can demonstrate high purity being free or substantially free of foreign substances such as agents used to release articles from a mold. Furthermore, methods of the present invention, in some embodiments, permit the design and fabrication of sintered porous polymeric articles having customized structures. In one embodiment, methods of the present invention provide implants, such as craniofacial and maxillofacial implants, tailored to the physical parameters of an implant site in a patient.

Laser Sintered Porous Polymeric Articles

In one embodiment, the present invention provides a laser sintered porous polymeric article having an average pore size ranging from about 10 µm to about 1 mm. In some embodiments, a laser sintered porous polymeric article has an average pore size ranging from about 100 µm to about 400 µm, from about 150 µm to about 300 µm, or from about 200 µm to about 250 µm. In another embodiment, a laser sintered porous polymeric article has an average pore size ranging from about 300 µm to about 400 µm or from about 400 µm to about 600 µm. In some embodiments, a laser sintered porous article has an average pore size of at least 20 µm. In some embodiments, a laser sintered porous article has an average pore size of at least 50 µm. In a further embodiment, a laser sintered porous polymeric article has an average pore size less than about 10 µm or greater than about 1 mm. In some embodiments, a laser sintered porous polymeric material comprises multidirectional and interconnected pores.

A laser sintered porous polymeric article, in some embodiments, has a porosity ranging from about 20 percent to about 60 percent, from about 30 percent to about 50 percent, from about 35 percent to about 40 percent, or from about 50 percent to about 60 percent. In another embodiment, a laser sintered porous polymeric article has a porosity less than about 20 percent or greater than about 60 percent. In one embodiment, a laser sintered porous article has a porosity of at least 20 percent.

In some embodiments, a laser sintered porous polymeric article comprises a single sintered polymeric layer. In other embodiments, a laser sintered porous polymeric article comprises a plurality of sintered polymeric layers. In some embodiments, each of the plurality of layers of a laser sintered porous polymeric article is constructed independently of any other layer. As a result, layers of a laser sintered porous polymeric article, in some embodiments, demonstrate different polymers, average pore sizes, and/or porosities.

In one embodiment, laser sintered porous polymeric articles of the present invention comprise polyolefins, polyamides, polyesters, polyurethanes, polyimides, polyacrylonitriles, polycarbonates, polymethylmethacrylate (PMMA), polytetrafluoroethylene (PTFE), polyvinylidene fluoride (PVDF), polyketones, polysulfones, polyetherimides, or combinations or copolymers thereof.

In some embodiments, a polyolefin comprises polyethylene, polypropylene, or combinations or copolymers thereof. Polyethylene, in one embodiment, comprises high density polyethylene (HDPE). High density polyethylene, as used herein, refers to polyethylene having a density ranging from about 0.92 g/cm$^3$ to about 0.97 g/cm$^3$. In some embodiments, high density polyethylene has a degree of crystallinity (% from density) ranging from about 50 to about 90. In another embodiment, polyethylene comprises ultrahigh molecular weight polyethylene (UHMWPE). Ultrahigh molecular weight polyethylene, as used herein, refers to polyethylene having a molecular weight greater than 1,000,000.

In another embodiment, polyketones comprise polyetherketone (PEK), polyetheretherketone (PEEK), or combinations thereof. Moreover, polysulfones, in some embodiments, comprise polyether sulfone (PES), polyphenyl sulfone, or combinations thereof.

In one embodiment, a laser sintered porous polymeric article comprises a polyethylene having any of the melt flow index values provided in Table 1. The melt flow index values provided in Table 1 were determined at 10 minutes under a 2.16 kg load at 190° C. as detailed in ASTM 1238-65.

TABLE 1

Melt Flow Index (MFI) Values of Polyethylene

| MFI Value |
| --- |
| less than 100 g |
| less than 50 g |
| less than 30 g |
| less than 15 g |
| less than 10 g |
| less than 5 g |
| less than 2 g |
| less than 1 g |

In another embodiment, a laser sintered porous polymeric article comprises a polypropylene having any of the melt flow index values provided in Table 2. The melt flow index values provided in Table 2 were determined at 10 minutes under a 2.16 kg load at 230° C. as detailed in ASTM 1238-65.

TABLE 2

Melt Flow Index (MFI) Values of Polypropylene

| MFI Value |
| --- |
| less than 100 g |
| less than 50 g |
| less than 30 g |
| less than 15 g |
| less than 10 g |
| less than 5 g |
| less than 2 g |

In another embodiment, a laser sintered porous polymeric article comprises a polyetheretherketone having any of the melt flow index values provided in Table 3. The melt flow index values provided in Table 3 were determined at 10 minutes under a 5 kg load at 379° C. as set forth in ISO 1133.

TABLE 3

Melt Flow Index (MFI) Values of PEEK

| MFI Value |
| --- |
| less than 100 $cm^3$ |
| less than 50 $cm^3$ |
| less than 30 $cm^3$ |
| less than 15 $cm^3$ |
| less than 10 $cm^3$ |
| less than 5 $cm^3$ |
| less than 2 $cm^3$ |

In another embodiment, a laser sintered porous polymeric article further comprises at least one inorganic material. In some embodiments, a laser sintered porous polymeric article further comprises a plurality of particles of at least one inorganic material. Particles of an inorganic material can be dispersed throughout the polymeric matrix of a laser sintered porous article. In one embodiment, an inorganic material comprises a metal including, but not limited to, a transition metals such as titanium, silver, or mixtures thereof. In another embodiment, an inorganic material comprises surgical grade stainless steel, steel coated with titanium, titanium nitride, or titanium alloyed with other metals. In one embodiment, an inorganic material comprises hydroxyapatite. In some embodiments, an inorganic material comprises a glass. In some embodiments, a glass has a composition comprising by weight 45% $SiO_2$, 24.5% $Na_2O$, 24.5% CaO, and 6% $P_2O_5$. In some embodiments, a glass comprises BIOGLASS® commercially available from NovaBone Products, LLC of Alachua Fla.

In other embodiments, suitable inorganic materials comprise calcium phosphates. Calcium phosphates, in some embodiments, have a calcium to phosphorus atomic ratio ranging from 0.5 to 2.0. Non-limiting examples of calcium phosphates suitable for use in laser sintered porous articles comprise amorphous calcium phosphate, monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), α-tricalcium phosphate, β-tricalcium phosphate, hydroxyapatite (OHAp), poorly crystalline hydroxyapatite, tetracalcium phosphate (TTCP), heptacalcium decaphosphate, calcium metaphosphate, calcium pyrophosphate dihydrate, calcium pyrophosphate, carbonated calcium phosphate, or mixtures thereof. In another embodiment, suitable inorganic material comprise barium sulfate and/or other imaging contrast agents. In some embodiments, an inorganic material comprises a mixture of any of the foregoing metals, alloys, calcium phosphates, contrast agents and/or glasses.

A laser sintered porous polymeric article, in some embodiments, comprises at least one inorganic material in an amount up to about 30 weight percent or from about 5 weight percent to about 20 weight percent. In some embodiments, a laser sintered porous polymeric article comprises at least one inorganic material in an amount ranging from about 10 weight percent to about 15 weight percent. In some embodiments a laser sintered porous polymeric article comprises at least one inorganic material in an amount less than about 1 weight percent or in an amount greater than about 30 weight percent. In one embodiment, a laser sintered porous polymeric article comprises at least one inorganic material in an amount less than about 0.1 weight percent.

In another aspect, the present invention provides a laser sintered porous polymeric article comprising a first layer and at least one additional layer, the first layer comprising a first polymeric material and the at least one additional layer comprising an additional polymeric material. In one embodiment, the first polymeric material and the additional polymeric material are the same. In another embodiment, the first polymeric material and the additional polymeric material are different. Polymers suitable for use as the first polymeric material and the additional polymeric material are consistent with those provided hereinabove.

In some embodiments, a laser sintered porous polymeric article comprising a first layer and at least one additional layer has an average pore size ranging from about 10 μm to about 1 mm. In other embodiments, the laser sintered porous article has an average pore size ranging from about 100 μm to about 400, from about 150 μm to about 300 μm, or from about 200 μm to about 250 μm. In another embodiment, a laser sintered porous polymeric article has an average pore size ranging from about 300 μm to about 400 μm or from about 400 μm to about 600 μm. In some embodiments, a laser sintered porous article has an average pore size of at least 20 μm. In a further embodiment, a laser sintered porous polymeric article comprising a first layer and at least one additional layer has an average pore size less than about 10 µm or greater than about 1 mm.

A laser sintered porous polymeric article comprising a first layer and at least one additional layer, in one embodiment, has a porosity ranging from about 20 percent to about 60 percent. In another embodiment, the laser sintered porous polymeric article has a porosity ranging from about 30 percent to about 50 percent, from about 35 percent to about 40 percent, or from about 50 percent to about 60 percent. In some embodiments, a laser sintered porous polymeric article has porosity less than about 20 or greater than about 60 percent. In one embodiments, a laser sintered porous article has porosity of at least 20 percent.

In another embodiment, a laser sintered porous polymeric article comprising a first layer and at least one additional layer comprises a porosity gradient. A porosity gradient is established, in some embodiments of the present invention, when the first layer of a laser sintered porous polymeric article has a porosity different than the at least one additional layer of the laser sintered porous polymeric article. In one embodiment, for example, the first layer has a porosity greater than the at least one additional layer. In another embodiment, the at least one additional layer has a porosity greater than the first layer. In some embodiments, the first layer and the at least one additional layer can independently demonstrate any of the porosities and pore sizes provided herein.

In some embodiments, the first and/or any additional layer is non-porous or substantially non-porous. In one embodiment, for example, a laser sintered porous polymeric article comprises a porous surface layer and a non-porous or substantially non-porous second layer. A non-porous or substantially non-porous second layer, in some embodiments, is the core of the laser sintered article. In such embodiments, the porous surface layer envelopes the non-porous core. In other embodiments, the porous surface layer partially covers the non-porous core.

A laser sintered porous polymeric article comprising a first layer and at least one additional layer, in some embodiments, further comprises at least one inorganic material. Inorganic materials suitable for use in embodiments of laser sintered porous polymeric articles comprising a first layer and at least one additional layer are consistent with the inorganic materials recited hereinabove. In one embodiment, a laser sintered porous polymeric article comprising a first layer and at least one additional layer comprises an inorganic material in an amount ranging from about 1 weight percent to about 30 weight percent, from about 5 weight percent to about 20 weight percent, or from about 10 weight percent to about 15 weight percent. In one embodiment, a laser sintered porous polymeric articles comprises at least one inorganic material in an amount less than about 0.1 weight percent.

In some embodiments, particles of an inorganic material are dispersed throughout the first layer and at least one additional layer of a laser sintered porous polymeric article. In another embodiment, a compositional gradient is established between the first layer and the at least one additional layer with respect to the distribution of the inorganic material. In one embodiment, for example, the first layer of the laser sintered porous polymeric article comprises a greater amount of an inorganic material than the at least one additional layer. In another embodiment, the at least one additional layer of the laser sintered porous polymeric article comprises a greater amount of the at least one inorganic material.

Laser sintered porous polymeric articles, in some embodiments of the present invention, are implants. In one embodiment, a laser sintered porous polymeric article is a non-load bearing implant. Non-load bearing implants, in some embodiments, comprise craniofacial implants or maxillofacial implants. In another embodiment, an implant is a load bearing implant. In some embodiments, a load bearing implant comprises hip implants or spinal implants.

The porous nature of laser sintered polymeric articles of the present invention is advantageous for implants as it can promote cellular in-growth. As provided herein, in some embodiments, laser sintered porous polymeric articles demonstrate porosity gradients. Porosity gradients within a laser sintered polymeric article can promote or assist cellular in-growth in selected areas of the implant. An implant comprising a laser sintered porous polymeric article, for example, may have a high porosity on surfaces where cellular in-growth is desired and low or no porosity on surfaces where cellular in-growth is not desired. As provided herein, a laser sintered porous polymeric article, in some embodiments, comprises porous layers and non-porous or substantially non-porous layers. As a result, laser sintered porous polymeric articles can be constructed to have porosity in regions of the article where cellular in-growth is desired and low or no porosity in regions of the article wherein cellular in-growth is not desired.

Moreover, as provided herein in some embodiments, laser sintered porous polymeric articles comprise compositional gradients. Compositional gradients can be used to enhance compatibility of implants comprising laser sintered porous polymeric articles of the present invention with various tissues in a human or animal body. In one embodiment, for example, an implant comprising a laser sintered porous polymeric article may have higher amounts of titanium and/or calcium phosphate particles on surfaces proximal or adjacent to bone tissue and lower amounts of titanium and/or calcium phosphate particles on surfaces distal from bone tissue. In a further embodiment, porosity and compositional gradients are used in conjunction to tailor the physical and chemical properties of an implant comprising a laser sintered porous polymeric article of the present invention to the physical and biochemical properties of an implant site in a patient.

Methods of Making Laser Sintered Porous Polymeric Articles

In another aspect, the present invention provides methods of making a laser sintered porous polymeric article. A method of making a laser sintered porous polymeric article, in one embodiment, comprises providing a first layer of particles of a first polymeric material and heating selected locations of the first layer with electromagnetic radiation to sinter particles of the first polymeric material to form a three-dimensional article, the three-dimensional article having a porosity of at least 20 percent. In another embodiment, the three-dimensional article has an average pore size ranging from about 10 µm to about 1 mm. In some embodiments, the three-dimensional article has an average pore size ranging from about 100 µm to about 400 µm, from about 150 µm to about 300 µm, or from about 200 µm to about 250 µm. In another embodiment, the three-dimensional article has an average pore size ranging from about 300 µm to about 400 µm or from about 400 µm to about 600 µm. In some embodiments, the three-dimensional article has an average pore size of at least 20 µm. In a further embodiment, the three-dimensional article has an average pore size less than about 10 µm or greater than about 1 mm.

Moreover, in some embodiments, the first layer of particles of a first polymeric material has a thickness greater than about 10 µm, greater than about 50 µm, greater than about 75 µm, greater than about 100 µm, greater than about 200 µm, or greater than about 500 µm. In one embodiment, the first layer of polymeric particles is heated prior to sintering with electromagnetic radiation.

A three-dimensional article produced according methods of the present invention, in some embodiments, has a porosity ranging from about 20 percent to about 60 percent, from about 30 percent to about 50 percent, from about 35 percent to about 40 percent, or from about 50 percent to about 60 percent. In another embodiment, a three-dimensional article has a porosity less than about 20 percent or greater than about 60 percent. In one embodiment, a three-dimensional article has a porosity of at least about 20 percent. In another embodiment, a three-dimensional article has a porosity of at least about 30 percent.

In some embodiments of methods of making a laser sintered porous polymeric material, electromagnetic radiation comprises visible electromagnetic radiation, infrared electromagnetic radiation, or combinations thereof. Moreover, in embodiments of methods of the present invention, electromagnetic radiation is supplied from a radiation source. In one embodiment, a radiation source comprises a laser. Lasers suitable for use in some embodiments of the present invention comprise gas lasers, such as a carbon dioxide ($CO_2$) laser, solid state lasers, such as a Nd:YAG laser, or semiconductor lasers, such as a laser diode. In some embodiments, the power of a laser ranges from about 30 watts to about 100 watts.

In some embodiments, a three-dimensional article produced according to methods of the present invention comprises a only a single sintered polymeric layer. In other embodiments, a three-dimensional article comprises a plurality of sintered polymeric layers.

In another embodiment, a method of making a laser sintered porous polymeric article comprises providing a first layer comprising particles of a first polymeric material mixed with particles of at least one inorganic material and heating selected locations of the first layer with electromagnetic radiation to sinter particles of the first polymeric material to form a three-dimensional article having particles of the at least one inorganic material dispersed therein. In some embodiments, the three-dimensional article having particles of at least one inorganic material dispersed therein has an average pore size and/or porosity consistent with the laser sintered porous polymeric articles provided hereinabove. Inorganic materials suitable for use in methods of the present invention are consistent with those provided hereinabove. A first layer comprising particles of a first polymeric material mixed with particles of at least one inorganic material, in some embodiments, has a thickness greater than about 50 µm, greater than about 75 µm, greater than about 100 µm, greater than about 200 µm, or greater than about 500 µm.

Selected locations of layers comprising polymeric particles, in some embodiments, are exposed to electromagnetic radiation for a time period ranging from less than about 1 second to about five minutes. Exposure time for individual layers of polymeric particles can be dependent on the cross-sectional area of the layer and the power as well as the number of scans provided by the source of the electromagnetic radiation, such as a laser. In some embodiments, a laser has a power of 30 watts, 50 watts, or 100 watts. The polymeric particles of selected locations of a layer exposed to electromagnetic radiation are heated to a temperature sufficient to sinter the polymeric particles. In embodiments wherein a non-porous layer is constructed, polymeric particles of selected locations of a layer exposed to electromagnetic radiation are heated to melt the particles to form a non-porous structure. In some embodiments, polymers having a high melt flow index are selected for layers having a non-porous or substantially non-porous structure.

In some embodiments, a method of making a laser sintered porous polymeric article further comprises providing at least one additional layer comprising particles of an additional polymeric material adjacent to the first layer and heating selected locations of the at least one additional layer with electromagnetic radiation to sinter particles of the additional polymeric material. The additional polymeric material, in some embodiments, is the same as the first polymeric material. In other embodiments, the additional polymeric material is different than the first polymeric material. In some embodiments, the at least one additional layer is heated prior to sintering with electromagnetic radiation.

Each additional layer comprising particles of an additional polymeric material, according to some embodiments of the present invention, is stacked upon the preceding layer in order increase the thickness of the laser sintered porous polymeric article. Sintered locations of each additional layer, in some embodiments, are selected to correspond with sintered locations of the preceding layer such that each additional layer and the preceding layer are fused together. Any number of additional layers may be stacked to produce a laser sintered porous polymeric article having any desired thickness. In some embodiments, each additional layer has a thickness of greater than about 10 µm, greater than about 50 µm, greater than about 75 µm, greater than about 100 µm, greater than about 200 µm or greater than about 500 µm.

Moreover, in some embodiments of methods of the present invention, the first layer has porosity greater than the at least one additional layer. In other embodiments, the at least one additional layer has a porosity greater than the first layer. A porosity gradient, in some embodiments, can be induced between the first layer and at least one additional layer by selecting polymeric particles of the first layer to be larger or smaller than the polymeric particles of the at least one additional layer. In another embodiment, a porosity gradient can be induced by heating one layer longer than the other layer. The at least one additional layer, for example, can be heated for a longer time period than the first layer to induce a porosity gradient wherein the first layer has a greater porosity than the at least one additional layer.

In some embodiments of methods of the present invention, the at least one additional layer further comprises particles of at least one inorganic material. In some embodiments, the first layer comprises a greater amount of an inorganic material than the at least one additional layer. In other embodiments, the at least one additional layer comprises a greater amount an inorganic material than the first layer.

Moreover, particles of a first polymeric material and particles of an additional polymeric material can comprise any of the polymers recited hereinabove as being suitable for use in laser sintered porous materials of the present invention. In some embodiments, particles of a first polymeric material and particles of an additional polymeric material are independently selected and have average sizes ranging from about 10 µm to about 5 mm, from about 50 µm to about 3 mm, from about 100 µm to about 1 mm, from about 200 µm to about 750 µm, from about 300 µm to about 600 µm, or from about 400 µm to about 500 µm. In some embodiments, particles of a first polymeric material and/or particles of an additional polymeric material have an average size ranging from about 400 µm to about 1 mm, from about 500 µm to about 800 µm, or from about 600 µm to about 750 µm.

In some embodiments of a method of making a laser sintered porous polymeric article, providing a layer of polymeric particles comprises disposing the polymeric particles in a sintering chamber. A sintering chamber, in some embodiments, is heated to a temperature near the melting point of the polymeric particles prior to heating selected locations of the layer of polymeric particles with electromagnetic radiation. The temperature to which the sintering chamber is heated prior to the selective application of electromagnetic radiation is dependent on the identity of polymeric particles provided to the chamber.

Additionally, in some embodiments, a method of making a laser sintered porous polymeric article further comprises heating the article subsequent to formation. In some embodiments, the laser sintered porous article, once formed, is heated to a temperature near or above the melting point of the first polymeric material and/or any additional polymeric material. Moreover, the time period for heating is dependent on the size of the article and, in some embodiments, ranges from about 30 second to about 60 minutes. A laser sintered porous article, in some embodiments, is heated in an oven. In some embodiments, a laser sintered porous article is covered or wrapped with a thermally conductive material during the heating. In one embodiment, a thermally conductive material comprises a metal foil such as, but not limited to, aluminum foil. In some embodiments, heating the laser sintered porous polymeric article increases the mechanical strength of the article.

Additionally, in some embodiments, a methods of making a laser sintered porous polymeric article further comprises smoothing one or more surfaces of the article. Smoothing one or more surfaces of a laser sintered porous polymeric article can be accomplished by a variety of processes, including tumbling, sanding, or combinations thereof.

In some embodiments, a laser sintered porous polymeric article produced by a method of the present invention comprises an implant. Laser sintered porous polymeric articles of the present invention, in some embodiments, are non-load bearing implants such as craniofacial implants or maxillofacial implants. Implants according to some embodiments of the present invention may be used to cover any portion of the cranium, such as the frontal, occipital, parietal, and temporal bones, portions thereof, or combinations thereof. Implants of the present invention, may also be used to repair or replace other bones of the face, such as the maxilla and mandible.

Methods of Treating Patients

In another aspect, the present invention provides methods of treating patients in need of an implant. In one embodiment, a method of treating a patient in need of an implant comprises creating a three-dimensional image of the implant area in the patient, converting the three-dimensional image into a format compatible with a selective laser sintering apparatus, providing a first layer of particles of a first polymeric material, heating locations of the first layer selected according to the three-dimensional image with electromagnetic radiation to sinter particles of the first polymeric material to form a three-dimensional implant having an average pore size ranging from about 10 µm to about 1 mm, and inserting the three-dimensional implant in the implant area.

In some embodiments, the three-dimensional implant has an average pore size ranging from about 100 µm to about 400 µm, from about 150 µm to about 300 µm, or from about 200 µm to about 250 µm. In another embodiment, a laser sintered porous polymeric article has an average pore size ranging from about 300 µm to about 400 µm or from about 400 µm to about 600 µm. In some embodiments, a laser sintered porous polymeric article has an average pore size of at least about 20 µm. In another embodiment, the three-dimensional implant has an average pore size less than about 10 µm or greater than about 1 mm. Three-dimensional implants of the present invention can be inserted into the implant area of a patient according to techniques known to one of skill in the art.

A three-dimensional implant, in some embodiments of methods of the present invention, has a porosity ranging from about 20 percent to about 60 percent, from about 30 percent to about 50 percent, from about 35 percent to about 40 percent, or from about 50 percent to about 60 percent. In another embodiment, a three-dimensional implant has a porosity less than about 20 percent or greater than about 60 percent. In some embodiments, a three-dimensional implant has a porosity of at least about 20 percent. In another embodiment, a three-dimensional implant has a porosity of at least about 30 percent.

In some embodiments of methods of treating a patient, electromagnetic radiation comprises visible electromagnetic radiation, infrared electromagnetic radiation, or combinations thereof. Moreover, in embodiments of methods of the present invention, electromagnetic radiation is supplied from a radiation source. In one embodiment, a radiation source comprises a laser. Lasers suitable for use in some embodiments of the present invention comprise gas lasers, such as a carbon dioxide (CM laser, solid state lasers, such as a Nd:YAG laser, or semiconductor lasers, such as a laser diode.

Creating a three-dimensional image of an implant site, in some embodiments, comprises imaging the implant site with computed tomography and/or other imaging techniques known to one of skill in the art. Moreover, converting the three-dimensional image into a format compatible with a selective laser sintering apparatus, in some embodiments, comprises converting the three-dimensional image into computer-readable format operable to be read by a processing unit of a selective laser sintering apparatus. Selective laser sintering apparatus suitable for use in methods of the present invention are commercially available from EOS GmbH of Munich, Germany and 3D Systems, Inc. of Rock Hill, S.C.

Implants for use in methods of treating patients in need thereof, in some embodiments, comprise at least one additional layer of sintered polymeric particles. As a result, a method of treating a patient in need of an implant, in some embodiments, further comprises providing at least one additional layer of particles of an additional polymeric material adjacent to the first layer and heating locations of the at least one additional layer selected according to the three-dimensional image with electromagnetic radiation to sinter particles of the additional polymeric material. In some embodiments, the first polymeric material and the additional polymeric material are the same. In other embodiments, the first polymeric material and the additional polymeric material are different. Moreover, in some embodiments, particles of at least one inorganic material are mixed with particles of the first polymeric material and/or particles of the additional polymeric material prior to sintering.

In some embodiments of a method of treating a patient, providing a layer of polymeric particles comprises disposing the polymeric particles in a sintering chamber. A sintering chamber, in some embodiments, is heated to a temperature near the melting point of the polymeric particles prior to heating selected locations of the layer of polymeric particles with electromagnetic radiation. The temperature to which the sintering chamber is heated prior to the selective application of electromagnetic radiation is dependent on the identity of polymeric particles provided to the chamber.

The first polymeric layer, in some embodiments of methods treating a patient in need of an implant, has a thickness greater than about 10 µm, greater than about 50 µm, greater than about 75 µm, greater than about 100 µm, greater than about 200 µm, or greater than about 500 µm. Moreover, each additional layer comprising an additional polymeric material, in some embodiments, has a thickness greater than about 50 µm, greater than about 75 µm, greater than about 100 µm, greater than about 200 µm, or greater than about 500 µm.

Particles of a first polymeric material and particles of an additional polymeric material, in some embodiments, are independently selected and can comprise any of the polymers recited hereinabove as being suitable for use in laser sintered porous materials of the present invention.

In some embodiments, particles of a first polymeric material and particles of an additional polymeric material are independently selected and have average sizes ranging from about 10 µm to about 5 mm, from about 50 µm to about 3 mm, from about 100 µm to about 1 mm, from about 200 µm to about 750 µm, from about 300 µm to about 600 µm, or from about 400 µm to about 500 µm. In some embodiments, particles of a first polymeric material and/or particles of an additional polymeric material have an average size ranging from about 400 µm to about 1 mm, from about 500 µm to about 800 µm, or from about 600 µm to about 750 µm.

In some embodiments, a three-dimensional implant comprises a non-load bearing implant such as a craniofacial implant or a maxillofacial implant. In some embodiments, a three-dimensional implant comprises a non-load bearing implant such as a hip implant or a spinal implant. Moreover, a patient, in some embodiments, comprises a human patient. In other embodiment, a patient comprises an animal including, but not limited to, a domesticated animal such as a cat, dog, or horse.

Embodiments of the present invention are further illustrated in the following non-limiting examples.

Example 1

Preparation of a Selectively Laser Sintered Porous Polymeric Implant

A laser sintering apparatus model number EOSINT P 385 from EOS GmbH was used to fabricate the laser sintered porous polymeric implant. A computer file encoding an image of a quarter of a human skull was transferred to the processing unit of the EOS selective laser sintering apparatus. HDPE particles having an average size of about 500 µm and a melt flow index of 2 g per 10 minutes under a 21.6 kg load at 190° C. were loaded into the sample powder chamber of the laser sintering apparatus. The polyethylene particles were pre-heated to about 70° C. in the sample chamber in an argon atmosphere. The sintering chamber was heated to a temperature of about 120° C. and pre-loaded with a layer of polyethylene particles having a thickness of about 1 cm. The sintering chamber was lowered down 600 µm. A first layer of polyethylene particles from the sample chamber was applied to the sintering chamber, the first layer of polyethylene particles having a thickness of about 600 µm. The first layer of polyethylene particles was heated under argon in the sintering chamber to about 120° C. with an infrared source. After the first layer of polyethylene particles reached 120° C., locations of the layer selected according to the image of the quarter human skull were sintered under argon by exposure to a 50 watt $CO_2$ laser. Exposure time to the $CO_2$ laser was determined according to the cross-sectional area of the layer and the number of laser scans.

After selected locations of the first layer of polyethylene particles were sintered by the laser, the sintering chamber was lowered down 600 µm and an additional layer of polyethylene particles from the sample chamber was disposed over the first layer. The additional layer had a thickness of about 600 µm. The additional layer was heated under argon to about 120° C. with an infrared source. After the additional layer of polyethylene particles reached 120° C., locations of the additional layer selected according to the image of the quarter skull were sintered under argon by exposure to a 50 watt $CO_2$ laser. Exposure time to the $CO_2$ laser was determined according to the cross-sectional area of the layer and the number of laser scans.

Figure 2:
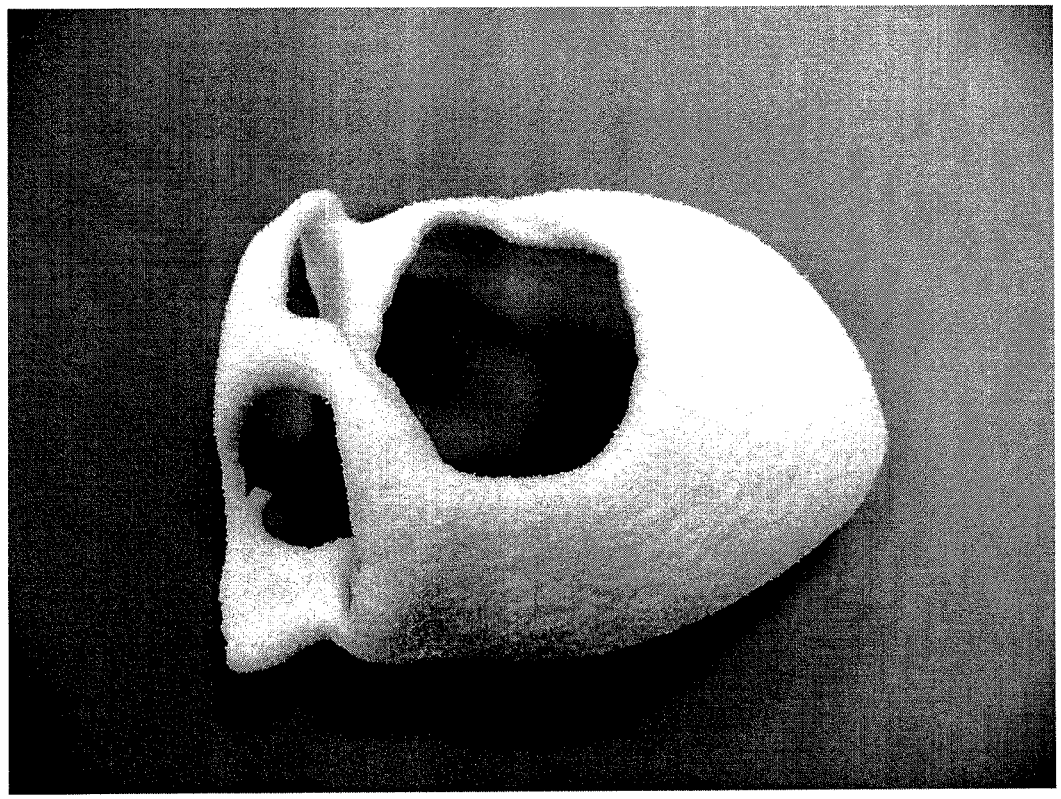
FIG. 2 illustrates a perspective view of a laser sintered porous polymeric article according to one embodiment of the present invention.
Figure 3:
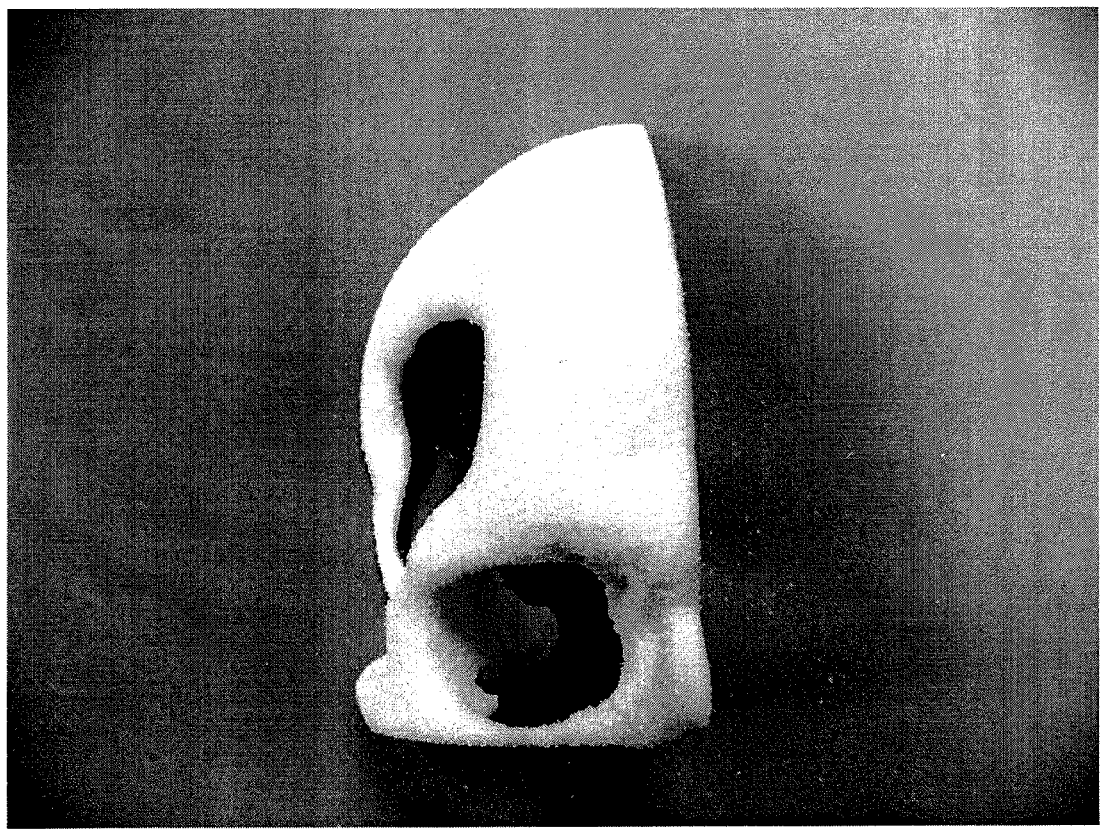
FIG. 3 illustrates a perspective view of a laser sintered porous polymeric article according to one embodiment of the present invention.

The process of adding and selectively sintering additional layers of polyethylene particles was repeated until the fabrication of the quarter skull was complete. After completion of the laser sintered porous polymeric implant, the temperature of the sintering chamber was lowered to room temperature and the implant was removed from the sintering chamber. FIGS. 1-3 provide perspective views of the quarter skull implant produced in the present example. The laser sintered porous polymeric implant had an average pore size of about 153 µm and a porosity of about 33%.

Example 2

Preparation of a Selectively Laser Sintered Porous Polymeric Implant

A laser sintering apparatus model number EOSINT P 385 from EOS GmbH is used to fabricate the laser sintered porous polymeric implant. A computer file encoding an image of a quarter of a human skull is transferred to the processing unit of the EOS selective laser sintering apparatus. A powder mixture comprising 90 weight percent HDPE particles having an average size of about 500 µm and a melt flow index of 2 g per 10 minutes under a 21.6 kg load at 190° C. and 10 weight percent hydroxyapatite particles (BABI-HAP-G10) is loaded into the sample powder chamber of the laser sintering apparatus. The particulate mixture is pre-heated to about 70° C. in the sample chamber in an argon atmosphere. The sintering chamber is heated to a temperature of about 120° C. and pre-loaded with a layer of polyethylene particles having a thickness of about 1 cm. The sintering chamber is lowered down 600 µm. A first layer of the particulate mixture is applied to the sintering chamber, the first layer of the particulate mixture having a thickness of about 600 µm. The first layer of the particulate mixture is heated under argon in the sintering chamber to about 120° C. with an infrared source. After the first layer of the particulate mixture reaches 120° C., locations of the layer selected according to the image of the quarter human skull are sintered under argon by exposure to a 50 watt $CO_2$ laser. Exposure time to the $CO_2$ laser is determined according to the cross-sectional area of the layer and the number of laser scans.

After selected locations of the first layer of the particulate mixture are sintered by the laser, the sintering chamber is lowered down 600 µm and an additional layer of particulate mixture from the sample chamber is disposed over the first layer. The additional layer has a thickness of about 600 µm. The additional layer of the particulate mixture is heated under argon to about 120° C. with an infrared source. After the additional layer of the particulate mixture reaches 120° C., locations of the additional layer selected according to the image of the quarter skull are sintered under argon by exposure to a 50 watt $CO_2$ laser. Exposure time to the $CO_2$ laser is determined according to the cross-sectional area of the layer and the number of laser scans.

The process of adding and selectively sintering additional layers of the particulate mixture is repeated until the fabrication of the quarter skull is complete. After completion of the laser sintered porous polymeric implant, the temperature of the sintering chamber is lowered to room temperature and the implant is removed from the sintering chamber. The laser sintered porous polymeric implant has an average pore size of about 150 µm and a porosity of about 35%.

Example 3

Preparation of a Selectively Laser Sintered Porous Polymeric Implant Having a Porosity Gradient A laser sintering apparatus model number EOSINT P 385 from EOS GmbH is used to fabricate the laser sintered porous polymeric implant. A computer file encoding an image of a quarter of a human skull is transferred to the processing unit of the EOS selective laser sintering apparatus. HDPE particles having an average size of about 500 µm and a melt flow index of 2 g per 10 minutes under a 21.6 kg load at 190° C. are loaded into the sample powder chamber of the laser sintering apparatus. The polyethylene particles are pre-heated to about 70° C. in the sample chamber in an argon atmosphere. The sintering chamber is heated to a temperature of about 120° C. and is pre-loaded with a layer of polyethylene particles having a thickness of about 1 cm. The sintering chamber is lowered down 600 µm. A first layer of polyethylene particles is applied to the sintering chamber, the first layer of polyethylene particles having a thickness of about 600 µm. The first layer of polyethylene particles is heated under argon in the sintering chamber to about 120° C. with an infrared source. After the first layer of polyethylene particles reaches 120° C., locations of the layer selected according to the image of the quarter human skull are sintered under argon by exposure to a 50 watt $CO_2$ laser. Exposure time to the $CO_2$ laser is determined according to the cross-sectional area of the layer and the number of laser scans.

After selected locations of the first layer of polyethylene particles are sintered by the laser, the sintering chamber is lowered down 600 µm and an additional layer of polyethylene particles was disposed over the first layer. The additional layer has a thickness of about 600 µm. The additional layer is heated under argon to about 120° C. with an infrared source. After the additional layer of polyethylene particles reaches 120° C., locations of the additional layer selected according to the image of the quarter skull are sintered under argon by exposure to a 50 watt $CO_2$ laser. Exposure time to the $CO_2$ laser is determined according to the cross-sectional area of the layer and the number of laser scans.

The process of adding and selectively sintering additional layers of polyethylene particles is repeated until the fabrication of the lower half of the quarter skull is complete. After completion of the lower half of the skull implant, HDPE particles having an average size of about 150 µm and a melt flow index of 2 g per 10 minutes under a 21.6 kg load at 190° C. are loaded into a second sample powder chamber of the laser sintering apparatus. The sintering chamber is lowered down 200 µm and a layer of polyethylene particles having an average size of about 150 µm from the second sample chamber is applied to the sintering chamber comprising the half completed quarter skull. The layer of polyethylene particles from the second sample chamber has a thickness of about 200 µm and is heated under argon to 120° C. Once the layer of polyethylene particles from the second sample chamber reaches 120° C., locations of the layer selected according to the image of the quarter skull are sintered under argon by exposure to a 50 watt $CO_2$ laser. Exposure time to the $CO_2$ laser is determined according to the cross-sectional area of the layer and the number of laser scans.

After selected locations of the layer of polyethylene particles from the second sample chamber are sintered, the sintering chamber is lowered 200 µm. An additional layer of polyethylene particles from the second sample chamber is applied to the laser sintering chamber. The additional layer has a thickness of about 200 µm and is heated under argon to 120° C. Once the additional layer of polyethylene particles reaches 120° C., locations of the additional layer selected according to the image of the quarter skull are sintered under argon by exposure to a 50 watt $CO_2$ laser. Exposure time to the $CO_2$ laser is determined according to the cross-sectional area of the layer and the number of laser scans.

The process of adding and selectively sintering additional layers of polyethylene particles from the second sample chamber is repeated until the upper half of the quarter skull is completed. After completion of the upper half of the skull implant, the sample chamber is cooled to room temperature and the implant is removed from the chamber. The lower half of the implant fabricated from polyethylene particles having an average diameter of about 500 µm has a porosity of about 33% and an average pore size of about 150 µm. The upper half of the implant fabricated from polyethylene particles having an average diameter of about 150 µm has a porosity of about 40% and an average pore size of about 40 µm. In some embodiments, the lower half the skull implant corresponds to the interior side of the implant while the upper half corresponds to the exterior side of the implant. As demonstrated herein, porosities of the interior and exterior implant surfaces can be varied according to the type and application of the implant.

Example 4

Preparation of a Selectively Laser Sintered Porous Polymeric Implant

A laser sintering apparatus model number EOSINT P 385 from EOS GmbH is used to fabricate the laser sintered porous polymeric implant. A computer file encoding an image of a quarter of a human skull is transferred to the processing unit of the EOS selective laser sintering apparatus. Polypropylene particles having an average size of about 400 µm and a melt flow index of 2 g per 10 minutes under a 21.6 kg load at 230° C. is loaded into the sample powder chamber of the laser sintering apparatus. The polypropylene particles are pre-heated to about 70° C. in the sample chamber in an argon atmosphere. The sintering chamber is heated to a temperature of about 165° C. and pre-loaded with a layer of polypropylene particles having a thickness of about 1 cm. The sintering chamber is lowered down 600 µm. A first layer of polypropylene particles from the sample chamber is applied to the sintering chamber, the first layer of polypropylene particles having a thickness of about 600 µm. The first layer of propylene particles is heated under argon in the sintering chamber to about 165° C. with an infrared source. After the first layer of polypropylene particles reaches 165° C., locations of the layer selected according to the image of the quarter human skull are sintered under argon by exposure to a 50 watt $CO_2$ laser. Exposure time to the $CO_2$ laser is determined according to the cross-sectional area of the layer and the number of laser scans.

After selected locations of the first layer of polypropylene particles are sintered by the laser, the sintering chamber is lowered down 600 µm and an additional layer of polypropylene particles from the sample chamber is disposed over the first layer. The additional layer has a thickness of about 600 µm. The additional layer is heated under argon to about 165°

C. with an infrared source. After the additional layer of polypropylene particles reaches 165° C., locations of the additional layer selected according to the image of the quarter skull are sintered under argon by exposure to a 50 watt $CO_2$ laser. Exposure time to the $CO_2$ laser is determined according to the cross-sectional area of the layer and the number of laser scans.

The process of adding and selectively sintering additional layers of polypropylene particles is repeated until the fabrication of the quarter skull is complete. After completion of the laser sintered porous polymeric implant, the temperature of the sintering chamber is lowered to room temperature and the implant was removed from the sintering chamber. The laser sintered porous polymeric implant has an average pore size of about 120 μm and a porosity of about 35%.

Example 5

Heating of a Selectively Laser Sintered Porous Polymeric Implant

THE SELECTIVELY LASER SINTERED POROUS POLYMERIC IMPLANT OF Example 1 was subjected to further heat treatment as provided herein. The implant was wrapped in aluminum foil and placed in a convection oven for 10 minutes at a temperature of 170° C. The resulting article had an average pore size of about 150 μm and a porosity of about 30 percent.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A laser sintered porous polymeric article comprising:
a core having a first polymeric material, a first porosity, and a first amount of inorganic material;
an outer surface layer at least partially enveloping the core, the outer surface layer having a second polymeric material, a second porosity, and a second amount of inorganic material; and
an intermediary layer including a third polymeric material and being disposed between the outer surface layer and the core, the intermediary layer having both a porosity gradient and a compositional gradient, the porosity gradient having a range of porosities extending between the first porosity and the second porosity and the compositional gradient having a range of amounts of inorganic material extending between the first amount of inorganic material and the second amount of inorganic material,
wherein the core is substantially non-porous and the outer surface layer is substantially porous,
wherein the second amount of inorganic material is greater than the first amount of inorganic material, and
wherein the inorganic material comprises a mixture of at least two components selected from the group consisting of a metal, metal alloy, calcium phosphate, stainless steel and glass.

2. The laser sintered porous polymeric article of claim 1, wherein at least one of the first, second, and third polymeric materials comprises a polyolefin.

3. The laser sintered porous polymeric article of claim 2, wherein the polyolefin comprises polyethylene, polypropylene, or copolymers thereof.

4. The laser sintered porous polymeric article of claim 3, wherein the polyethylene comprises high density polyethylene, ultrahigh molecular weight polyethylene, or mixtures thereof.

5. The laser sintered porous polymeric article of claim 1, wherein the porosity of the outer surface layer is at least 20 percent.

6. The laser sintered porous polymeric article of claim 1, wherein the article is an implant.

7. The laser sintered porous polymeric article of claim 6, wherein the implant is a craniofacial implant or a maxillofacial implant.

8. The laser sintered porous polymeric article of claim 1, wherein the article comprises an interconnected pore structure.

9. A method of producing the laser sintered porous polymeric article of claim 1 comprising the steps of:
providing a first layer of particles of the first polymeric material, the first layer of particles including the first amount of inorganic material;
providing a second layer of particles of the second polymeric material, the second layer of particles including the second amount of inorganic material;
successively providing additional layers of particles of the third polymeric material, the successive layers of particles including the range of amounts of inorganic material which extend between the first amount of inorganic material and the second amount of inorganic material;
heating selected locations of the first, second, and additional layers to sinter particles of the first, second, and third polymeric materials to form a three dimensional article,
wherein the core of the article comprises the first layer of particles, the outer surface layer comprises the second layer of particles, and the intermediary layer comprises the additional layers of particles, and
wherein the three dimensional article has a porosity of at least about 20 percent.

10. The method of claim 9, wherein heating comprises exposing the selected locations to electromagnetic radiation.

11. The method of claim 10, wherein the electromagnetic radiation comprises visible radiation, infrared radiation, or combinations thereof.

12. The method of claim 9, wherein the three dimensional article has an average pore size of at least about 20 μm.

13. The method of claim 9, wherein the three-dimensional article comprises an implant.

14. The method of claim 13, wherein the implant comprises a craniofacial implant or a maxillofacial implant.

15. The method of claim 9, wherein the three dimensional article comprises an interconnected pore structure.

16. An implant comprising:
a first region having a first polymeric material, a first porosity, and a first amount of inorganic material, wherein the combination of the first porosity and the first amount of inorganic material promotes bone in-growth;
a second region having a second polymeric material, a second porosity, and a second amount of inorganic material, wherein the combination of the second porosity and the second amount of inorganic material resists bone in-growth; and
a third region including a third polymeric material and having both a porosity gradient and a compositional gradient, the porosity gradient having a range of porosities extending between the first porosity and the second porosity and the compositional gradient having a range of amounts of inorganic material extending between the first amount of inorganic material and the second amount of inorganic material, wherein the compositional gradient has a higher amount of inorganic material in regions adjacent to bone tissue and a lower amount of inorganic material in regions distal to bone tissue, wherein the first amount of inorganic material in the first region is higher than the second amount of inorganic material in the second region in order to promote tissue compatibility between the first region and an adjacent region of bone, wherein the second region is substantially non-porous and the first region has a higher porosity than the second region, and wherein the inorganic material comprises a mixture of at least two components selected from the group consisting of a metal, metal alloy, calcium phosphate, stainless steel, and glass.

17. The implant of claim 16, wherein at least one of the first and second regions has an average pore size of at least about 20 µm.

18. The implant of claim 16, wherein at least one of the first and second regions has an average pore size ranging from about 10 µm to about 1 mm.

19. The implant of claim 16, wherein the inorganic material of at least one of the first, second, and third regions is present in an amount up to about 30 weight percent of the implant.

20. The implant of claim 16, wherein the second region is a core of the implant.

21. The implant of claim 16, wherein the first porosity of the first region is at least 20 percent.

22. A method of treating a patient in need of the implant of claim 16 comprising the steps of:

creating a three-dimensional image of the implant area;

converting the three-dimensional image into a format compatible with a selective laser sintering apparatus;

providing a first layer of particles of the first polymeric material, the first layer of particles including the first amount of inorganic material;

providing a second layer of particles of the second polymeric material, the second layer of particles including the second amount of inorganic material;

successively providing additional layers of particles of the third polymeric material, the successive layers of particles including the range of amounts of inorganic material which extend between the first amount of inorganic material and the second amount of inorganic material;

heating locations of the first, second, and additional layers according to the three-dimensional image to sinter particles of the first, second, and third polymeric materials to form a three dimensional implant, wherein the first region of the implant comprises the first layer of particles, the second region comprises the second layer of particles, and the third region comprises the additional layers of particles, the three dimensional implant having a porosity of at least about 20 percent; and implanting the three-dimensional implant into the implant area.

23. The method of claim 22, wherein the implant has an average pore size of at least about 20 µm.

24. The method of claim 22, wherein the implant comprises a multidirectional and interconnected pore structure.

25. The method of claim 22, wherein the implant comprises a craniofacial implant or a maxillofacial implant.

* * * * *